(12) United States Patent
Mor

(10) Patent No.: US 9,144,520 B2
(45) Date of Patent: Sep. 29, 2015

(54) NONINVASIVE DETECTION OF MECONIUM IN AMNIOTIC FLUID

(71) Applicant: Gideon Mor, Ramat Gan (IL)

(72) Inventor: Gideon Mor, Ramat Gan (IL)

( * ) Notice: Subject to any disclaimer, the term of this patent is extended or adjusted under 35 U.S.C. 154(b) by 388 days.

(21) Appl. No.: 13/742,649

(22) Filed: Jan. 16, 2013

(65) Prior Publication Data

US 2013/0165816 A1 Jun. 27, 2013

Related U.S. Application Data

(63) Continuation-in-part of application No. PCT/IL2012/050243, filed on Jul. 11, 2012.

(30) Foreign Application Priority Data

Jul. 14, 2011 (IL) .......................................... 214096

(51) Int. Cl.
```
A61M 1/00        (2006.01)
A61F 13/42       (2006.01)
A61B 10/00       (2006.01)
A61F 13/505      (2006.01)
A61B 5/00        (2006.01)
```
(52) U.S. Cl.
CPC ................ *A61F 13/42* (2013.01); *A61B 5/4294* (2013.01); *A61B 5/4362* (2013.01); *A61B 10/0048* (2013.01); *A61F 13/505* (2013.01); *A61B 2503/02* (2013.01)

(58) Field of Classification Search
CPC ............................. A61F 13/505; A61F 13/42
USPC .......................................... 604/318; 600/584
See application file for complete search history.

(56) References Cited

U.S. PATENT DOCUMENTS

| | | | |
|---|---|---|---|
| 5,172,693 A | 12/1992 | Doody |
| 5,361,759 A | 11/1994 | Genevier et al. |
| 5,425,377 A | 6/1995 | Caillouette |
| 5,514,598 A | 5/1996 | Doody |
| 5,713,351 A | 2/1998 | Billings et al. |
| 5,919,644 A | 7/1999 | Adachi et al. |
| 6,044,284 A | 3/2000 | Eisenfeld et al. |
| 6,503,198 B1 | 1/2003 | Aronowtiz et al. |

(Continued)

FOREIGN PATENT DOCUMENTS

| | | | |
|---|---|---|---|
| CA | 1009550 A1 | 5/1977 |
| GB | 2353357 A | 2/2001 |

(Continued)

OTHER PUBLICATIONS

Goldenberg et al., Carinoembryonic antigen present in meconium: The basis of a possible new diagnostic test of fetal distress, American Journal of Obstetrics and Gynecology, May 1, 1972, vol. 113, #1.

(Continued)

*Primary Examiner* — Brian Szmal
(74) *Attorney, Agent, or Firm* — Daniel J. Swirsky; AlphaPatent Associates Ltd.

(57) ABSTRACT

Meconium stained amniotic fluid can indicate intrauterine fetal distress. The invention provides a system and method for detecting meconium in released amniotic fluid in pregnant women, including a collection body such as a hygienic pad, having a meconium detector. This invention is designed to be employed mainly by a lay person at home; it also may provide possible etiologies for fetal distress.

20 Claims, 9 Drawing Sheets

(56) References Cited

U.S. PATENT DOCUMENTS

| | | |
|---|---|---|
| 7,541,177 B2 | 6/2009 | Kritzman et al. |
| 2005/0131287 A1 | 6/2005 | Kaylor et al. |
| 2010/0324391 A1 | 12/2010 | Kostenich et al. |

FOREIGN PATENT DOCUMENTS

| | | |
|---|---|---|
| JP | 5123324 B2 | 5/1993 |
| JP | 5203644 B2 | 8/1993 |
| WO | 9902985 A1 | 1/1999 |
| WO | 0004822 A1 | 2/2000 |
| WO | 3007997 A1 | 1/2003 |
| WO | 2009050711 A2 | 4/2009 |
| WO | 2010150804 | 12/2010 |
| WO | 2011151597 | 8/2011 |

OTHER PUBLICATIONS

Lolis et al., Carnioembryonic antigen in high risk pregnancies, International Journal of Gynaecology and Obstetrics, 1984, 22: 5-9.

Rani K. Measurement of bile acid in serum and bile with arylamine-glass-bound 3alpha-hydroxysteriod dehydrogenase and diaphorase. Analytical Biochemistry, vol. 332, No. 1, 1, Sep. 1, 2004.

Sarandakou et al. Expression of CEA, CA-125 and SCC antigen by biological fluids associated with pregnancy, European Journal of Obstetrics and Gynecology and Reproductive Biology, 44 (1992): 215-220.

Phupong and Sonthirathi, Placental alpha-microglobulin-1 rapid immunoassay for detection of premature rupture of membranes, Journal of Obstetrics and Gynaecology Research, Jan. 2012, pp. 226-230, vol. 38, No. 1, Japan Society of Obstetrics and Gynecology, Blackwell Publishing Asia Pty Ltd.

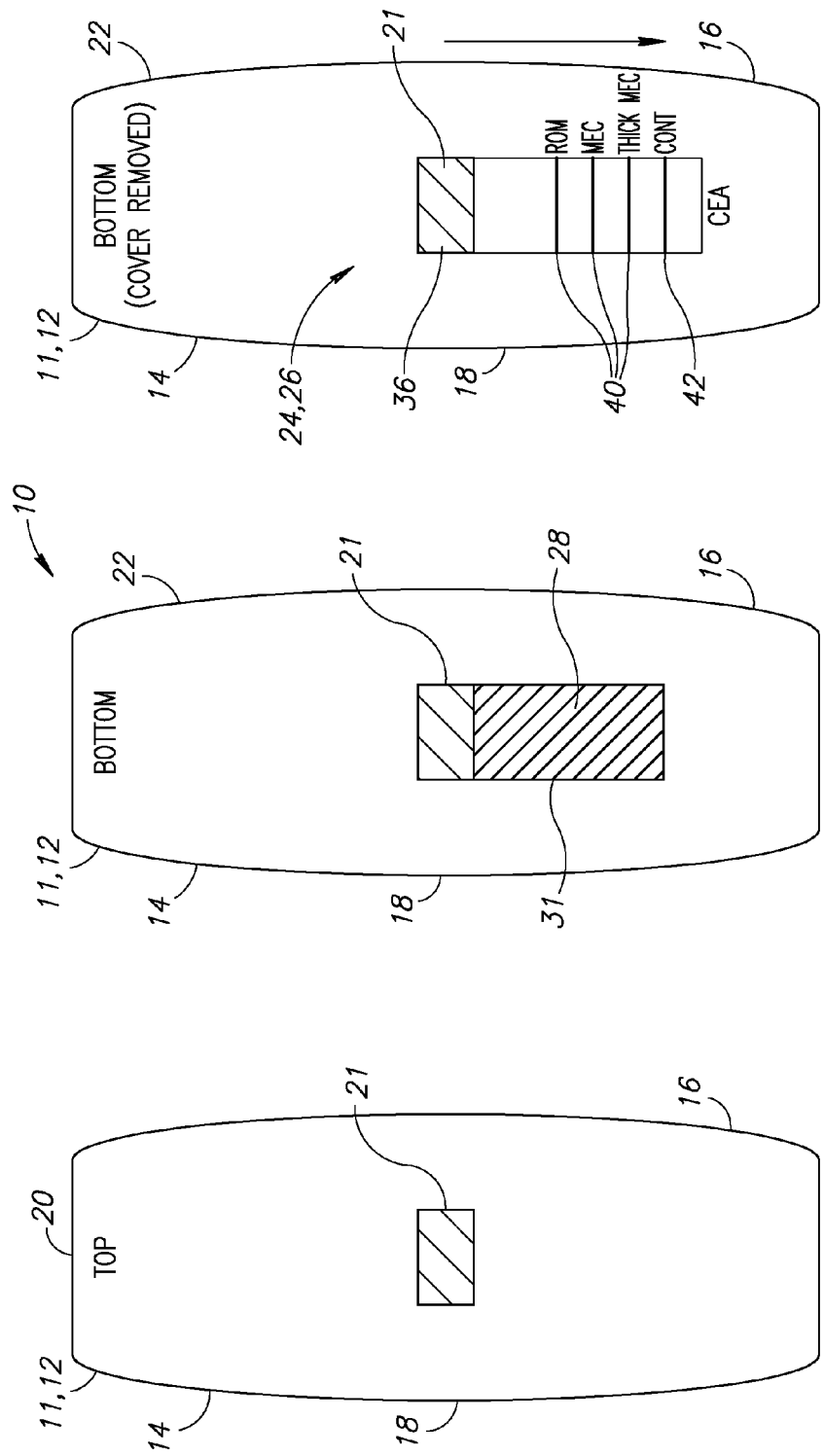

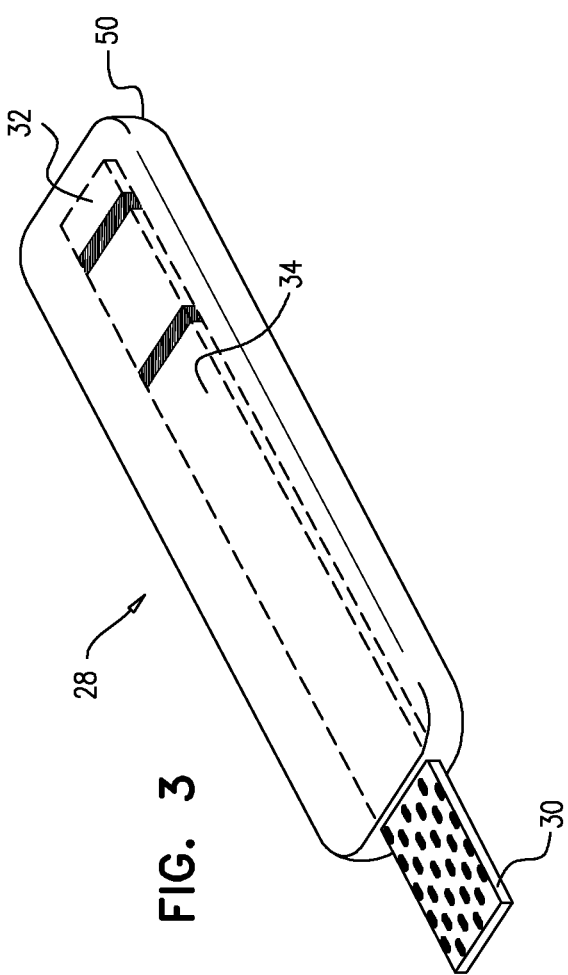

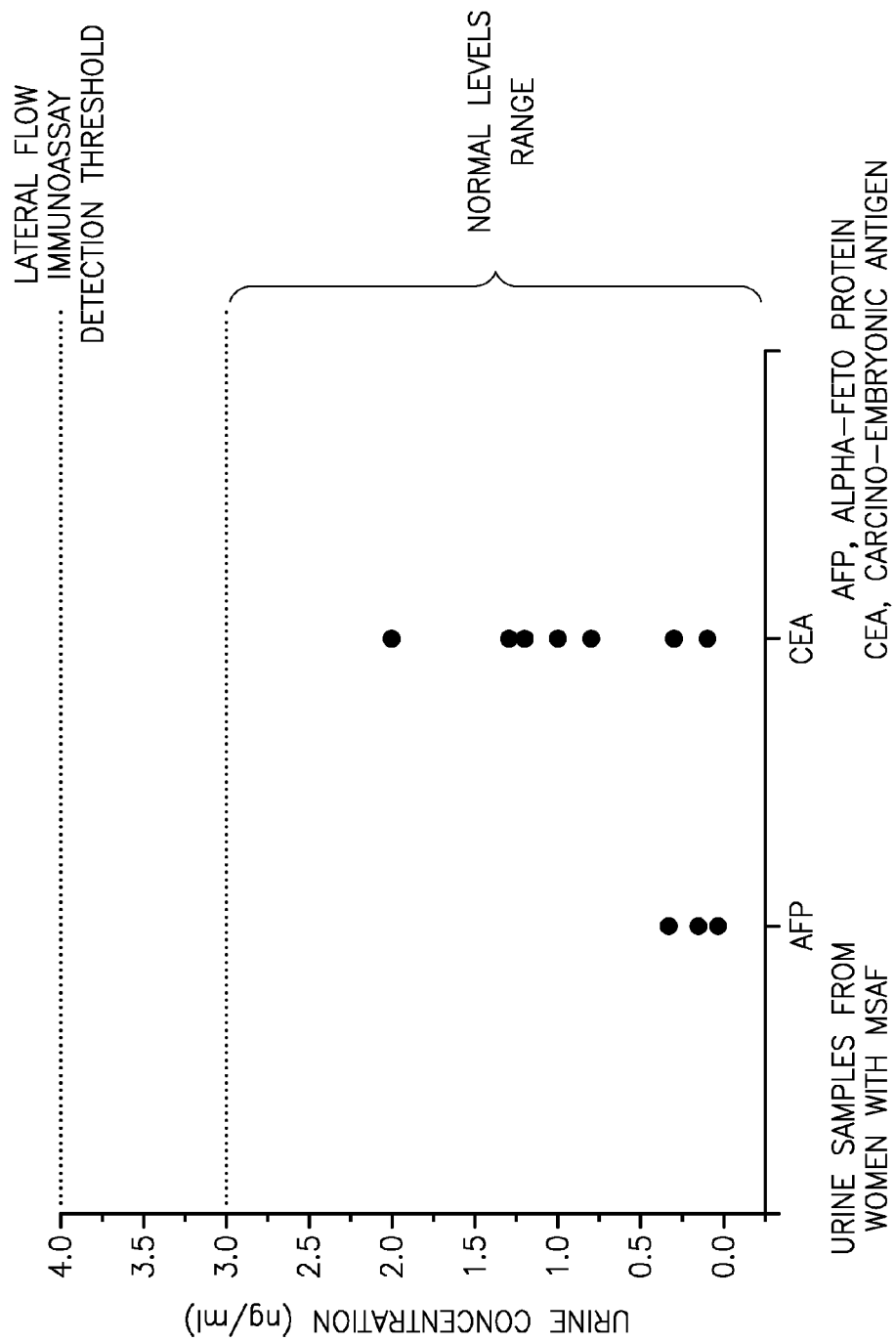

NONINVASIVE DETECTION OF MECONIUM IN AMNIOTIC FLUID

CROSS-REFERENCE TO RELATED APPLICATIONS

This application is a continuation-in-part of International Application No. PCT/IL2012/050243, filed on Jul. 11, 2012, which claims the benefit of priority of Israel Patent Application No. 214,096, filed on Jul. 14, 2011, and which are incorporated herein by reference in their entirety.

FIELD OF THE INVENTION

The present invention relates to a system and method for detecting meconium in released amniotic fluid in pregnant women.

BACKGROUND OF THE INVENTION

The colon of a fetus during gestation fills with meconium, the fetal feces comprising bile and its metabolites, gastrointestinal and pancreatic secretions, mucus, cellular debris, swallowed vernix caseosa, and blood. In a significant minority of births, the fetus ceases to be continent and excretes meconium into the amniotic fluid. It is important to be aware of such an occurrence for the future mother and for the obstetrics personnel.

The fetus may pass stool to the amniotic fluid in response to stress (e.g., hypoxemia) and then inhale it into the lungs. Fetal stool, meconium, is toxic in the lungs, it can obstruct airways, and also does harm by other mechanisms, resulting in meconium aspiration syndrome (MAS). Meconium aspiration may occur before, during, and after labor. About 13% of all live births are complicated by meconium-stained amniotic fluid (MSAF), and about 30,000 develop MAS annually in the United States, leading to the death of 1000 children. MSAF is associated with an increased risk for perinatal complications during labor and delivery (e.g., low Apgar score, higher risk for cesarean section, and higher admission rate to neonatal intensive care unit. MSAF is considered to be a marker for possible fetal compromise. Prenatal detection of meconium in the amniotic fluid can alert a caregiver or patient to intrauterine fetal distress and might have an important role in reducing the incidence and consequences of MAS, fetal hypoxemia, and cerebral palsy. Moreover, when meconium concentration is high—designated herein as thick meconium, the amniotic fluid has a dark green opaque color. Heavy (thick) MSAF may indicate worse fetal/neonatal prognosis than light (thin) MSAF.

There is a consensus that a pregnant woman with MSAF should be carefully evaluated for fetal well-being in order to reduce the chances of irreversible damage to the fetus/newborn. To date, a number of invasive and non-invasive methods and devices are known to identify MSAF. Amniocentesis is an invasive sampling procedure removing a small volume of the amniotic liquid for in vitro testing. U.S. Pat. No. 5,361,759 describes an invasive method for detection of undesired components, including meconium, in amniotic fluid by absorbance spectroscopy of a sample of amniotic fluid acquired by penetrating the amniotic sac. U.S. Pat. No. 5,713,351 describes an invasive method for the detection of meconium in amniotic fluid by penetrating the amniotic sac with a probe and withdrawing amniotic fluid through the lumen of the probe into an observation chamber. Amnioscopy is a less invasive technique, enabling direct observation of the forebag of an amniotic sac to look for meconium staining; it may help in detecting heavy staining by meconium, but milder cases remain undetected, and the method may require an undesirable degree of cervical dilation. U.S. Pat. No. 5,172,693 describes the detection of meconium in the amniotic sac by detecting fluorescence of the bilirubin component of meconium, placing a probe against the uterine wall and irradiating the amniotic fluid through the body tissues by excitation light, leading to characteristic fluorescence of eventual meconium components in vivo. US 2010/0324391 describes a device for detecting meconium in amniotic fluid by fluorescent measurement of zinc coproforphyrin in vivo. U.S. Pat. No. 6,044,284 relates to an apparatus for measuring the concentration of meconium in amniotic fluid by employing optical sensors measuring the fluid transmittance in vivo. The above approaches are characterized by physical or optical penetration into the amniotic sac. U.S. Pat. No. 5,514,598 describes a non-invasive method to detect MSAF: a specific meconium protein (14 kilodaltons) can be detected by immunological techniques.

All approaches described above must be employed by professional personnel and, therefore, limit their use to medical facilities. As a matter of fact, high quality fetal wellbeing monitoring is still restricted to skilled personnel (e.g., ultrasonographic fetal heart rate tracing, biophysical profiling, and amniotic fluid indexing).

Rupture of the amniotic sac membranes may occur throughout almost the whole pregnancy period. When rupture of membranes (ROM) occurs, umbilical cord (UC) prolapse (0.5 percent of all pregnancies) can be one of the biggest threats to the fetus. UC prolapse occurs when a UC loop precedes the leading part of the fetus (during spillage of amniotic fluid from the uterine cavity). During this process the UC loop may be compressed and result in imminent fetal asphyxia. In a significant minority of term pregnancies (37-40 gestational weeks) 10-15% of women arrive at the hospital with their 'water already broken'. ROM and the associated severe complications (e.g., UC compression, placental abruption) may occur at home, away from a medical facility. Failure to recognize and immediately treat these complications may result in fetal death. A well-established possible indicator for these complications is MSAF.

To date, there is no simple accurate method or device that enables home detection of MSAF by lay people. Furthermore, nowadays MSAF can be detected at home by the naked eye only. However, in a significant number of events MSAF may be bloody or may be lightly stained and therefore not detectable by the naked eye. Another important aspect is the ability to identify the etiology for MSAF (and the possible fetal distress) at home by lay people, as well as the potential severity of the MSAF. To date, there is no simple method or device enabling such a thing. It is an object of this invention to enable the detection of MSAF by lay people.

Thus, there is a need for: a) Providing a method of detecting MSAF without penetration into the amniotic sac; b) Providing a sensitive and specific method and kit for detecting MSAF (including bloody or lightly stained MSAF) without employing complex analytical tools or devices; c) Providing a method and a kit for detecting MSAF that can be employed by unskilled users at home; d) Providing a platform for identifying etiologies for fetal distress after ROM has occurred; e) Providing an inexpensive home kit that will reduce medical costs by early identification of fetal distress; and (f) Providing a method and kit for differentiating between thick and thin MSAF.

SUMMARY OF THE INVENTION

There is thus provided, in accordance with embodiments of the present invention, a system for detection of meconium in amniotic fluid. The system includes a collection body for collecting a body fluid released from a vaginal opening of a pregnant woman, and a meconium detector positioned in the collection body configured for detecting presence of meconium in the collected body fluid.

In embodiments of the present invention, the collection body may be a hygienic pad, an underwear, a tampon or an applicator. The collection body may include an absorbent portion configured to absorb a body fluid. The collection body may also include a fluid identifier for identifying the body fluid. In some embodiments, the meconium detector may include an immunoassay strip for detecting components of meconium, such as carcino-embryonic antigen (CEA). Thresholds for CEA may help to determine presence of meconium and more specifically presence of light or heavy meconium. Presence of relatively low CEA concentration may also be an indicator for presence of amniotic fluid.

In some embodiments, the meconium detector is embedded within the collection body, and in other embodiments, the meconium detector may be external to the collection body. For example, the meconium detector may include one or multiple reagents in a vial, which can react with the collected body fluid after collection thereof.

The present invention provides several advantages.

1. After ROM occurs there may be a prolonged amniotic fluid outflow. The fluid may be "meconium free" initially, and later on become MSAF. The present invention provides the ability to detect the presence of normal amniotic fluid and to detect when and if it changes MSAF. The ability to detect actual meconium secretion provides real time information on possible ongoing fetal distress. The knowledge that clear amniotic fluid becomes MSAF may significantly affect the medical management.

2. In some instances, an event of "water break" at home can be massive and become a transient, one-time event. In this case, when the pregnant woman arrives at a medical center, the physician may fail to detect any fluid coming out of the cervical canal/vagina. Under these circumstances MSAF can be missed, and different (or wrong) medical management will ensue. The present invention provides the ability to "catch" a transient, one-time event of MSAF secretion at home.

3. Artificial ROM for labor induction (employed by medical personnel) may expose MSAF presence. However, frequently MSAF is mixed with blood, mucus, and vernix, which make its detection difficult (even by professional experienced personnel). This invention provides a sensitive method and kit that enables bedside detection of MSAF even when it is mixed with other substances.

4. US 2010/0324391 and others describe a device for detecting MSAF inside an intact sac before ROM. The present invention may provide a complementary solution, which may serve as a complete approach for MSAF detection before and after ROM, and until birth.

The present invention may provide a platform of etiology(ies) for fetal distress. For example, uncontrolled Diabetes Mellitus (gestational, type 1, or type 2) is one of the leading causes of intrauterine fetal death during the third trimester. Information on the amniotic fluid sugar level may help with the assessment and the emergent management of the diabetic pregnant woman with MSAF. High amniotic fluid sugar level may point to the cause for MSAF and fetal distress. Other life-threatening events may comprise significant maternal or fetal bleeding. Another example is ROM resulting in meconium-free amniotic fluid outflow, stained with maternal blood (a normal condition), followed by MSAF with fetal blood (a condition indicating placental abruption and fetal asphyxia). This change is not detected by the naked eye. Employing colorimetric reactions for glucose, fetal hemoglobin, maternal hemoglobin, etc., together with continuous monitoring of MSAF appearance, provides an added value of early etiology detection. In this way, critical time can be saved upon arriving at the appropriate medical center.

Unless otherwise defined, all technical and scientific terms used herein have the same meaning as commonly understood by one of ordinary skill in the art to which this invention belongs. Although methods and materials similar or equivalent to those described herein can be used in the practice or testing of the embodiments of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of various embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several embodiments of the invention may be embodied in practice.

In the drawings:

FIGS. 2A-2C are schematic illustrations of a hygienic pad for prenatal detection of meconium including a lateral flow immunochromatographic assay in accordance with another embodiment of the present invention;

FIG. 3 is a schematic illustration of a strip of the assays of FIGS. 1C and 2C, including a protective cover;

FIG. 5C is a graphical illustration showing results of detection of CEA and alpha-fetoprotein (AFP) in urine samples of women with meconium-stained amniotic fluid (MSAF), in accordance with embodiments of the present invention.

Figure 1C:
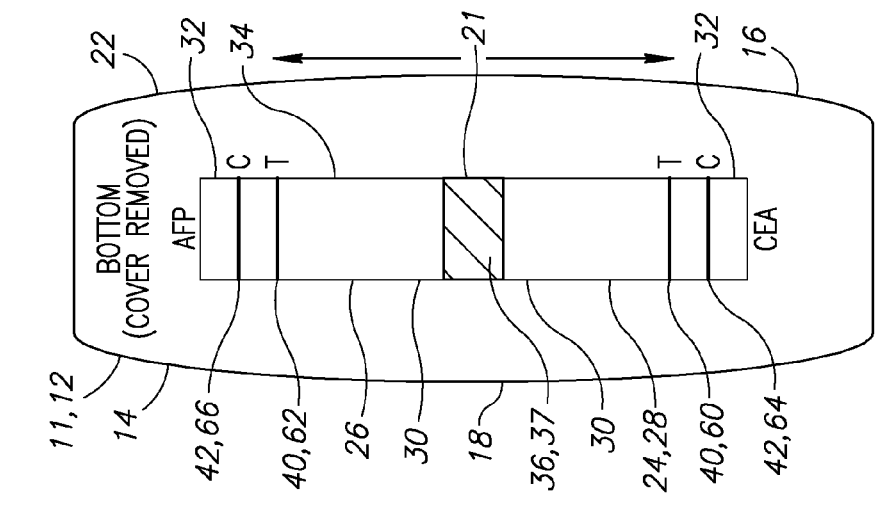
FIGS. 1A-1C are schematic illustrations of a hygienic pad for prenatal detection of meconium including a lateral flow immunochromatographic assay in accordance with one embodiment of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

The present invention relates to a system for detection of meconium in amniotic fluid, including a collection body and a meconium detector. The collection body may be a hygienic pad, specially designed underwear, a tampon, an applicator, or other means for collecting fluid released from a vaginal opening of a pregnant woman. The collection body may have one or multiple patches or absorbent portions, which are spatially defined areas for absorbing body fluid and eventually detecting in the body fluid components of meconium and/or of amniotic fluid. Patches may be impregnated with a composition for detecting at least one component typically found in body fluids or in meconium, or alternatively may be configured for adding such composition later while reacting with the components. Reactions may occur in the collection body or after transferring relevant components of the collection body to a detection device. Body fluids include amniotic fluid and other vaginal fluids. Components to be detected may include typical components of vaginal fluids or undesired components associated with any problems during pregnancy, for example, leaked amniotic fluid, presence of meconium in the fluid, infection, and bleeding. The collection body of the present invention is aimed particularly at detecting meconium in the amniotic fluid, but also at detecting leaked amniotic fluid, and at detecting various indicative components in vaginal fluid, wherein the collection body may be pre-impregnated with reagents producing indicative changes in the presence of examined components. It is an additional feature of the present invention that the system may be useful for detecting thick meconium and for differentiating between thick and thin meconium.

Figure 1B:
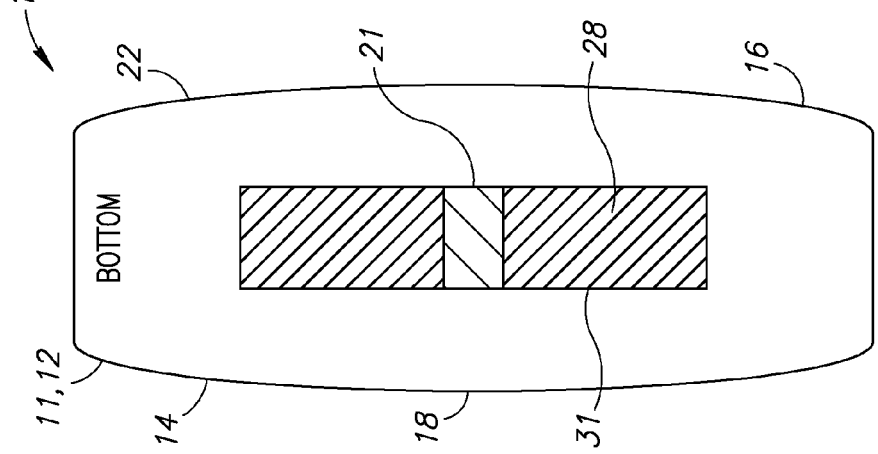
Figure 1A:
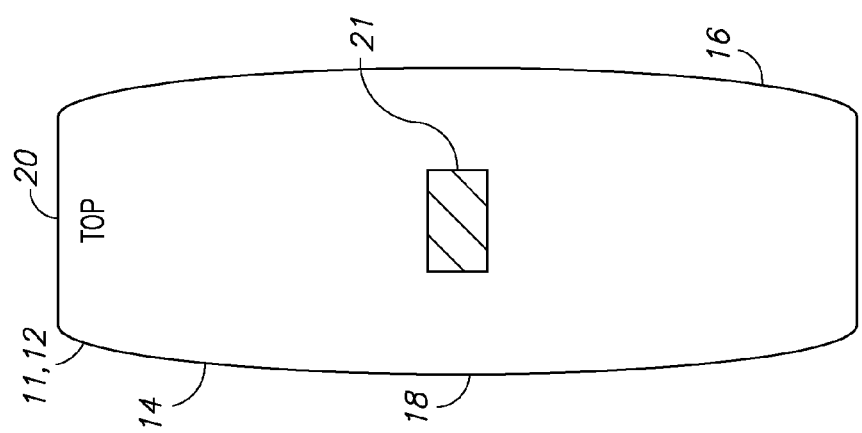

Reference is now made to FIGS. 1A-1C, which are schematic illustrations of a system 10 for detecting meconium in amniotic fluid, in accordance with embodiments of the present invention. It is a feature of the present invention that system 10 is capable of detecting meconium-containing fluid with enough specificity and sensitivity that a pregnant woman may be directed to consult her doctor or go urgently to the hospital in order to be managed as a "meconium positive" high risk pregnancy.

System 10 includes a collection body 11, which in the present embodiment is a hygienic pad 12 having a first end 14, a second end 16 opposite first end 14, and a middle section 18 connecting first and second ends 14 and 16. Hygienic pad 12 further includes a top portion 20 and a bottom portion 22 on an opposite side of top portion 20, ie, on an underside of pad 12. FIG. 1A is an illustration of top portion 20, and FIGS. 1B and 1C are illustrations of bottom portion 22. Top portion 20 is the side of pad 12 which faces the body orifice (ie, the vagina), and collects fluid discharged therefrom. Bottom portion 22 is situated on the opposite side, adjacent to the underwear, and in some embodiments adhesive thereto. Hygienic pad 12 further includes at least one absorbent portion 21, which may be, for example, a patch or a portion of hygienic pad 12 so designated. Absorbent portion 21 is configured to absorb a body fluid. Absorbent portion 21 comprises absorbent material such as, cellulose or fiber-based materials (e.g. Whatman 3MM Chr paper, GE Health care Life Sciences, Piscataway, N.J., USA). Absorbent portion 21 may be positioned at or near first end 14, second end 16 or middle section 18 and may be relatively small or large depending on the preferred sample size. Absorbent portion 21 may extend through pad 12 from top portion 20 to bottom portion 22, as shown in FIGS. 1A and 1B. System 10 further includes a meconium detector 24 positioned in hygienic pad 12. Meconium detector 24 is configured for detecting presence of meconium in the absorbed body fluid. In some embodiments, system 10 further includes a fluid identifier 26. Fluid identifier 26 is configured to identify the absorbed body fluid. For example, the body fluid may be amniotic fluid, urine, blood etc., and fluid identifier 26 is configured to identify which of these body fluids is present on hygienic pad 12. Hygienic pad 12 may be, for example, a panty liner. In additional embodiments, hygienic pad 12 may be incorporated into a panty or other undergarment. The structure of the pad comprises materials usual in personal panty liners, adherent shields, and hygienic pads.

In one embodiment, meconium detector 24 is a strip 28, such as a lateral flow immunochromatography assay strip used for detection of components such as proteins and glycoproteins. An example of strip 28 is shown in FIG. 3. Such assay strips are known in the art and may be obtained from, for example, CEA Serum Rapid Test (Strip 5 mm) RapiDip™ Instatest (Diagnostic Automation/Cortez Diagnostics, Inc., California, USA).

It should be readily apparent that strip 28 is not limited to the type disclosed herein, and that any suitable strip may be used. In the embodiment shown herein, strip 28 has a front tip 30 and a back tip 32, with a strip body 34 extending from front tip 30 to back tip 32. Strip 28 acts by capillary action, wherein fluid comes into contact with front tip 30, and is carried along strip body 34 to back tip 32. A chemical reaction occurs along strip body 34, causing elements of the fluid to be separated out and identified. In embodiments of the present invention, strip 28 includes a first reagent 36 for reacting with the fluid. First reagent 36 may be, for example, an antibody or series of antibodies, enzymes, a color pigment, multiple color pigments, color pigments attached to antibodies, color pigments sensitive to chemical products, or any other relevant reagent. Thus, a body fluid is absorbed into pad 12 at absorbent portion 21, at which point the body fluid comes into contact with front tip 30 of strip 28. Front tip 30 may already have first reagent 36 positioned therein, and when the body fluid comes into contact with first reagent 36, a combined substance of body fluid plus first reagent 36 may then extend, via capillary action, through strip body 34.

In embodiments of the present invention, meconium detector 24 includes a test indicator 40 and a control indicator 42, wherein test indicator 40 is configured to positively identify presence of meconium, and wherein control indicator 42 is configured to confirm reliability of the assay. For example, test indicator 40 may be a T band, as shown in FIG. 1C, and control indicator 42 may be a C band.

In some embodiments, fluid identifier 26 is also a strip 28, and comprises a second reagent 37 for reacting with the fluid, wherein second reagent 37 is configured to identify the fluid. In some embodiments, meconium detector 24 and fluid identifier 26 are comprised of two separate strips 28, wherein one strip comprises first reagent 36 and another strip comprises second reagent 37, and in other embodiments, a single strip 28 is configured to be used as both meconium detector 24 and fluid identifier 26 and comprises both first and second reagents 36 and 37.

A hygienic pad 12 in accordance with additional embodiments of the present invention is depicted schematically in FIGS. 2A-2C. In this embodiment, a single reagent is used to detect the presence of amniotic fluid, meconium, and thick meconium. In this embodiment, first reagent 36 is preferably CEA, but may be other reagents capable of identifying amniotic fluid, meconium and thick meconium. Different thresholds of CEA may be set for each of these indications. In this embodiment, multiple test indicators 40 may be used along with a single control indicator 42.

One or both of first and second reagents 36 and 37 may in some embodiments be present in collection body 11 from the beginning and in other embodiments may be added or partially added after collection body 11 has been contacted with the body fluid. In one embodiment, first reagent 36 is incorporated into collection body 11 while second reagent 37 is added or partially added during the process. In other embodiments, second reagent 37 is incorporated into collection body 11 while first reagent 36 is added or partially added during the process. Any combination of these options as well as additional reagents are included within the scope of the invention.

Returning now to FIG. 3, strip 28 may be protected by a transparent fluid-protective seal 50. Transparent fluid-protective seal 50 may be comprised of any hydrophobic material, such as nylon, polyester, etc. In some embodiments, fluid-protective seal 50 is positioned over strip body 34 and back tip 32, while front tip 30 is left unsealed. In this way, fluid absorbed into pad 12 at absorbent portion 21 will leak into strip 28 via front tip 30 and will be carried through strip body 28 in a single direction, from front tip 30 to back tip 32. The direction of flow may be important in ascertaining that a valid reaction occurs.

Returning now to FIGS. 1A-1C and to FIGS. 2A-2C, strip 28 or multiple strips 28 may be impregnated into hygienic pad 12. In some embodiments, as shown in FIG. 1B and in FIG. 2B, strip 28 is temporarily covered by a strip cover 31, which can be removed following exposure to the body fluid in order to read the results. System 10 is shown in FIG. 1C and FIG. 2C with strip cover 31 removed. Arrows indicate the liquid flow direction.

In some embodiments, as shown in FIG. 1C, a first strip 28 for CEA detection and a second strip 28 for AFP detection are positioned back-to-back within pad 12. It should be readily apparent that the positioning of strips 28 is not limited to the positions shown herein and that any suitable position for one or multiple strips 28 within pad 12 is included within the scope of the invention. Front tips 30 of strips 28 meet up in the middle of pad 12 at absorbent portion 21, and back tips 32 are on opposite sides of pad 12, with one back tip 32 at or near first end 14 and the other back tip 32 at or near second end 16. Thus, liquid is absorbed in the middle of pad 12 at absorbent portion 21, and through capillary action extends to both first end and second end 14 and 16 of pad 12 via each of strips 28. A first test indicator 40 is a first T band 60, designed to appear in the presence of CEA above a predetermined threshold, and a second test indicator 40 is a second T band 62, designed to appear in the presence of AFP. A first control indicator 42 is a first C band 64, designed to appear whether or not CEA is detected and to indicate that the first test is valid, and a second control indicator 42 is a second C band 66, designed to appear whether or not AFP is detected and to indicate that the second test is valid. Only when full sample lateral flow has occurred, as determined by the appearance of both C bands 64 and 66, can the results be interpreted. If sample diffusion is too slow, a drop of detergent/"sample buffer" can be added to the absorbent portion 21. Table 1 summarizes the possible results and interpretations.

TABLE 1

| Interpretation | AFP | | CEA | |
|---|---|---|---|---|
| | Band 60 T | Band 64 C | Band 62 T | Band 66 C |
| Full lateral flow has occurred (necessary for correct interpretation of the results) | − | + | − | + |
| Meconium-free amniotic fluid | + | + | − | + |
| Meconium stained amniotic fluid (MSAF) | + | + | + | + |

+, present;
−, absent;
T, test;
C, control.

When only C bands appear the sample fluid is not amniotic fluid; it can be urine due to urine leak/incontinence during pregnancy.

The use of both a meconium detector 24 and a fluid identifier 26, employing two different reactions, enhances the reliability of the system; false positive results, for example, are reduced. If the number of detectors and/or indicators is increased, it may make the system still sensitive and more specific.

In one embodiment of the present invention, detecting reagent 36 is a substance which is used to detect the presence of CEA in the body fluid. Such reagents are known in the art and include, for example, antibodies that are used to screen for malignancies, such as colorectal, pulmonary, mammary, and gynecologcal. It has been found experimentally in the present invention, as will be described in greater detail hereinbelow in the EXAMPLES, that a threshold for detecting CEA is indicative of presence of meconium. The threshold may be in a range of 300 ng/µl to 700 ng/µl, and in some embodiments, may be approximately 500 ng/µl. In other embodiments, detecting reagent 36 may be a substance used to detect bile acids. Other substances which may be indicative of the presence of meconium may include, for example, steroids having alcohol and/or carboxyl groups, enzymes such as pancreatic enzymes, brush border enzymes, or transporters for glucose, alanine, or methionine. The present invention is not limited to these indicators of meconium and to the detecting reagents specific to each of those. Any suitable substance for detecting meconium is included within the scope of the present invention.

In one embodiment of the present invention, second reagent 37 is a substance which is used to identify presence of alpha fetoprotein (AFP) in the body fluid. Such reagents are known in the art, such as, for example, antibodies for AFP. It has been shown that AFP detected at a threshold of at least 5 ng/µl is indicative of amniotic fluid. In other embodiments, as determined experimentally and presented in the EXAMPLES section, second reagent 37 may be CEA (with the same 5 ng/ml detection threshold). In other embodiments, fluid identifier 26 comprises an acid-base indicator. Since the pH of vaginal fluids is more acidic than the pH of amniotic fluid, it is possible to detect amniotic fluid based on pH. Thus, collection body 11 may be impregnated with an acid-base indicator, and the user may observe a color change in the presence of amniotic fluid. More specifically, the pH of amniotic fluid is generally between 7.0 and 7.5, and the pH of vaginal fluid without amniotic fluid is generally between 4.5 and 5.5. An alkaline pH, indicating a possible leakage of the amniotic fluid into the vagina, may be revealed in a method according to the invention by any acid-base indicator having a suitable pH range for its color change. Examples are bromocresol purple and nitrazine yellow. In some embodiments, in order to minimize false readings due to, for example, presence of blood or infections, fluid identifier 26 may alternatively or further include detection of other components of amniotic fluid such as carbohydrates and/or proteins, such as glucose, fructose, prolactin, alpha-fetoprotein (AFP), and diamine oxidase.

In some embodiments, the reactions employed in collection body 11 for detecting materials typical of the amniotic fluid and/or meconium may comprise reaction cascades, in which a substrate present in the body fluid of the user is absorbed in the collection body and provides a product in a first reaction that reacts in another reaction, while providing an indicative color change. Additional reactions may also be involved in the cascade. The reactions employed in the color reactions or in reaction cascades may comprise, for example, enzymatic reactions. The reactions employed in the color reactions or in reaction cascades may comprise interactions with specific antibodies. Advantageously, stabilized or immobilized enzymes, which are sufficiently stable at room temperature or at body temperature for the time needed, may be employed.

In one embodiment, detecting reagent 36 for detecting components of meconium may comprise multiple reagents. For example, detecting reagent 36 may comprise one reagent for reacting with a component of the meconium, and a second reagent for providing a color or other indicator.

In one embodiment, one reagent of detecting reagent 36 is 3-α-HSD, another one of the reagents in detecting reagent 36 is NBT, and yet another reagent within detecting reagent 36 is diaphorase. In this embodiment, 3-α-HSD reacting with bile acids present in meconium produces NADH. NADH can then be visualized by reacting with NBT in the presence of diaphorase. In one embodiment, some or all of detecting reagents 36 are incorporated in collection body 11 during its manufacture. In another embodiment, some or all of detecting reagents 36 are added onto an absorbent portion 21 such as a patch on hygienic pad 12 only after absorbing the body fluid. Some of the reagents, such as enzyme solutions, may be stored in a refrigerator before use, and may be part of a kit for detecting meconium in the released amniotic fluid.

In one embodiment, absorbent portions 21 include collection members for collecting the body fluid therein before performing at least one of the reactions, wherein the reactions are performed outside of collection body 11.

Figure 4A:
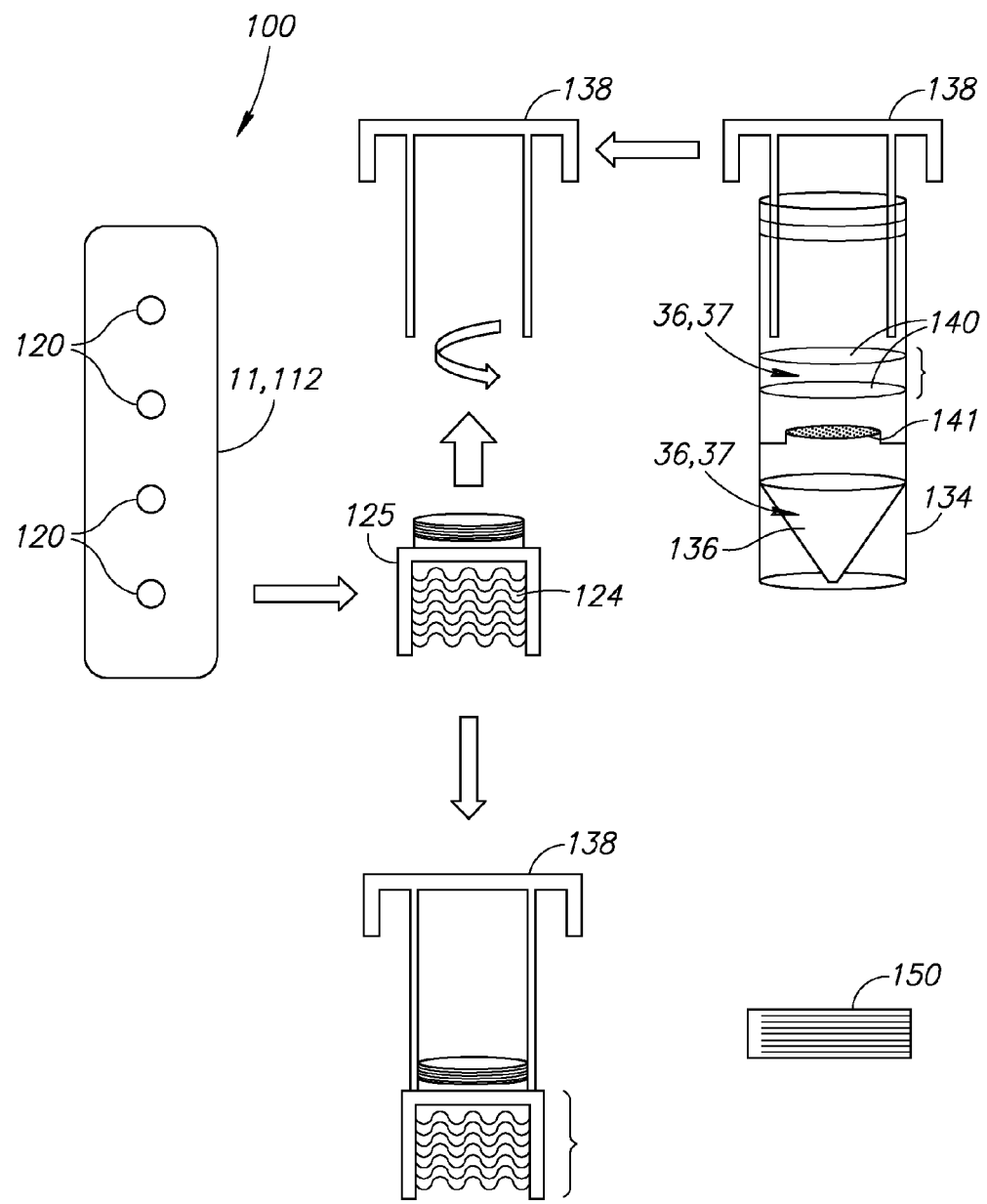
FIGS. 4A and 4B are schematic illustrations of a kit for prenatal detection of meconium according to one embodiment of the invention, the kit comprising a multi-patch hygienic pad with detachable collection members, and a reaction bottle.

Reference is now made to FIG. 4A, which is a schematic illustration of a kit 100 for prenatal detection of meconium in accordance with embodiments of the present invention. Kit 100 includes a collection body 11, which in the present embodiment is a multi-patch hygienic pad 112 comprising multiple patches 120, one or multiple reagents 36 to be used with at least one of multiple patches 120, and optionally a guide booklet 150. Patches 120 may comprise additional layers spatially stabilized within pad 112 supporting absorption or enabling localization of certain reagents. Materials known in the field, used as blotters or absorbers, acceptable for human use, are employed. Patches 120 may comprise layers separating reagents from direct contact with the user's body. In one embodiment, patches may have the form of test strips attached to the pad or within the pad structure, such as described above. In some embodiments, the outer layer of the pad may be torn off to enable better inspection of the color reagent after absorption of the body fluid. In some embodiments, patches 120 are not visible before using the pad, but their positions are denoted in the guide booklet 150 or manual.

In the embodiment shown herein, patches 120 include multiple detachable body fluid collection members 124. Collection member 124 may be, for example, a piece of material taken out of hygienic pad 112—for example, absorbent portion 21. The piece may be a preformed circle or other shape, for example, delimited with a weak line. In this embodiment, an external collection vial 125 may be used to place collection member 124 therein. Alternatively, collection member 124 may include a piece of absorbent material from pad 112 and a preformed structure, ie, collection vial, incorporated into the pad; such structure may be, for example, a plastic cylindrical body open on one or both ends. In either case, collection member 124 is designed to be removed from pad 112 and analyzed outside of pad 112 using other portions of kit 100.

Kit 100 further includes a detection device 134, which may be for example, a prepared test tube, vial or reaction bottle. An example of a detection device 134 is shown as a vial 136 in FIGS. 3A and 3B. In the embodiment shown herein, vial 136 includes a removable cap 138. Vial 136 further includes therein one or multiple detecting reagents 36 and/or identifying reagents 37. Reagents may be separated from one another by one or multiple partitions 140. Collection member 124 is introduced into vial 136 and thus brought into contact with detecting reagents 36 and/or identifying reagents 37. In vial 136, a visible color change indicates probable presence of components usually found in meconium or amniotic fluid, such as bile acids or CEA. In one example, vial 136 includes reagents 3-α-HSD, NBT, and diaphorase, which provide a color ranging from dark red to brown to black with bile acids.

In some embodiments, pad 112 includes an area with a pH sensitive surface that changes color when exposed to a relatively basic environment, indicating probable presence of the amniotic fluid; such an area may be on a surface of pad 112 or may be in one of patches 120, for example.

Kit 100 includes simple steps that can be easily performed at home by a lay person. Steps of a method of using kit 100 are now described. First, a pregnant subject continuously wears hygienic pad 112 ready to collect body fluid, eventually comprising escaped amniotic fluid, throughout the pregnancy term. The subject has detection device 134 (such as vial 136) with reagents therein. When body fluid is absorbed into pad 112, the subject removes the pad, and separates collection member 124 from pad 112. Cap 138 of vial 136 is removed, and collection member 124 is placed therein. Cap 138 is replaced onto vial 136. In embodiments of the present invention, replacing cap 138 results in breaking of partitions 140 located over a strainer 141 and subsequent mixing of reagents with the body fluids. For example, collection member 124, such as a blotter soaked with the body fluid, is placed onto a portion of vial having cap 138, and is then inserted into vial 136 while breaking partitions 140, thereby mixing reagents and the sample. If using, for example, the reaction system comprising 3-α HSD/NBT/diaphorase, the initial reaction color is yellow; when meconium is present the color changes to dark red/brown or black.

Reactions of the present invention may be performed in situ in the pad after addition of reagents, or in vitro after removing collection member 124 and transferring it to detection device 134. Detection device 134 may be provided as a separate item in kit 100 according to the invention, or it may be attached on or within pad 112, being prepared for later reaction, including active steps to be taken by the user of kit 100, for example further mixing of reagents with the body fluids.

Figure 4B:
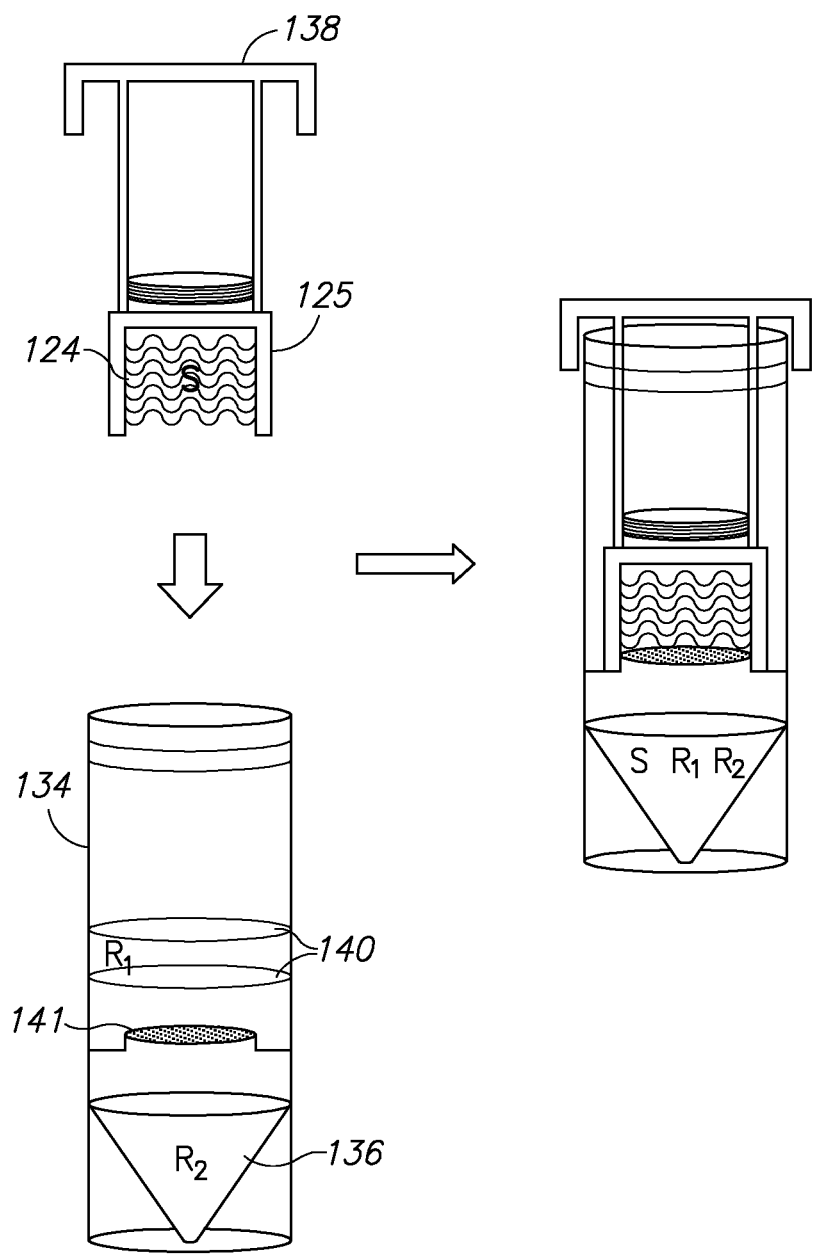

In one embodiment, collection member 124 includes absorbent material which is configured to increase the sorption of desired components from body fluids, such as bile acids, thereby eventually concentrating the components to be detected in collection member 124; said configuring may comprise special structural micro-arrangement of the sorbent, or inclusion of a highly sorbing blotter, or impregnation with a chemical that increases sorption of said desired component based, for example. The member is configured so that maximal sorption of required components occurs, while minimizing the contact of reagents with the skin. As schematically shown in FIG. 4B, sample S, entrapped in collection member 124 and connected to cap 138, is inserted into the opened detection device 134. Partitions 140 separating the reagents ($R_1$ and $R_2$) are broken as collection member 124 inside collection vial 125 moves down towards vial 136. The absorbent material with body liquid within collection member 124 may be squeezed over a strainer 141 placed below partition 140 to release the liquid from the fibers, thereby mixing the reagents with the sample, and starting the color reaction to be visually checked. Vial 136 may be at least partially transparent.

The system of the present invention can be easily employed by lay people at home. In some embodiments system 100 can be modified for the use with lateral flow immunoassays described in system 10. In some embodiments, the invention can be modified for the use of skilled medical personnel and utilized for additional testing. In some embodiments, system 10 comprises a probe such as a cylindrical probe insertable into the vagina (similar to a tampon) or by an applicator.

In some embodiments, system 10 may be used as a 'bedside test' and may assist the skilled/medical personnel in evaluating fetal distress and the associated etiologies.

EXAMPLES

Example 1

After obtaining informed consent, amniotic fluid specimens were collected from women in labor following rupture of membranes. Urine specimens were collected through a urethral catheter from time to time during and after labor.

Phase I of this experiment was performed in order to determine whether detectable levels of CEA and/or AFP may be found and whether these levels may have diagnostic value. Phase I was performed as follows: Amniotic fluid specimens were examined by medical personnel and were classified as clear amniotic fluid or meconium stained amniotic fluid (MSAF). Samples of clear amniotic fluid and samples of MSAF were then sent for quantitative measurement of CEA and AFP concentrations by ABBOTT AxSYM (a Microparticle Enzyme Immunoassay, ABBOTT Laboratories, Ill., USA).

Table 2 shows results of the quantitative measurements of CEA and AFP.

TABLE 2

| | SAMPLE TYPE | CEA ng/mL | AFP ng/mL |
|---|---|---|---|
| 1 | Clear AF | 91 | 140.75 |
| 2 | Clear AF | 145.6 | 196.69 |
| 3 | Clear AF | 118.3 | 291.12 |
| 4 | Clear AF | 209.3 | 150.51 |
| 5 | Clear AF | 127.4 | 226.84 |
| 6 | Clear AF | 309.4 | 167.86 |
| 7 | Clear AF | 72.8 | 83.48 |
| 8 | Clear AF | 18.2 | 35 |
| 9 | Clear AF | 109.2 | 360.33 |
| 10 | Clear AF | 45.5 | 121.03 |

TABLE 2-continued

| | SAMPLE TYPE | CEA ng/mL | AFP ng/mL |
|---|---|---|---|
| 1 | MSAF | 700.7 | 248.17 |
| 2 | MSAF | 2875.6 | 98.84 |
| 3 | MSAF | 2629.9 | 379.77 |
| 4 | MSAF | 627.9 | 265.52 |
| 5 | MSAF | 910 | 52.95 |
| 6 | MSAF | 2866.5 | 142.17 |
| 7 | MSAF | 3812.9 | 266.56 |
| 8 | MSAF | 2775.5 | 90.4 |
| 9 | MSAF | 1237.6 | 75.52 |
| 10 | MSAF | 1692.6 | 296.05 |
| 11 | MSAF | 4222.4 | 151.37 |
| 12 | MSAF | 2038.4 | 118.56 |
| 13 | MSAF | 646.1 | 109.84 |
| 14 | MSAF | 2912 | 165.3 |
| 15 | MSAF | 2993.9 | NA |
| 16 | MSAF | 4213.3 | 79.78 |
| 17 | MSAF | 6633.9 | 77.03 |
| 18 | MSAF | 576 | 200.1 |
| 19 | MSAF | 2047.5 | 56.65 |
| 1 | U-MSAF | 0.3 | 0.04 |
| 2 | U-MSAF | 0.8 | 0.15 |
| 3 | U-MSAF | 2 | 0.33 |
| 4 | U-MSAF | 0.1 | 0.02 |
| 5 | U-MSAF | 0.3 | 0.04 |
| 6 | U-MSAF | 1 | 0.03 |
| 7 | U-MSAF | 1.3 | 0.04 |
| 8 | U-MSAF | 1.2 | 0.03 |

In Table 2, Clear AF=Clear Amniotic Fluid; MSAF=Meconium Stained Amniotic Fluid; U-MSAF=Urine samples from women with MSAF; NA=Not Available. In summary, average CEA concentration was determined to be as follows:

Clear amniotic fluid: 125 ng/mL

Meconium stained amniotic fluid (MSAF): 2443 ng/mL

Urine from women with MSAF: 0.875 ng/mL (normal range is up to 3-5 ng/mL)

These results show that CEA levels are 20 times higher in MSAF than in clear amniotic fluid, and that CEA levels are normal in urine of women with MSAF.

Average AFP concentration was determined to be as follows:

Clear amniotic fluid: 177 ng/mL

Meconium stained amniotic fluid (MSAF): 160 ng/mL

Urine from women with MSAF: 0.085 ng/mL (normal range is up to 3-5 ng/mL)

Figure 5A:
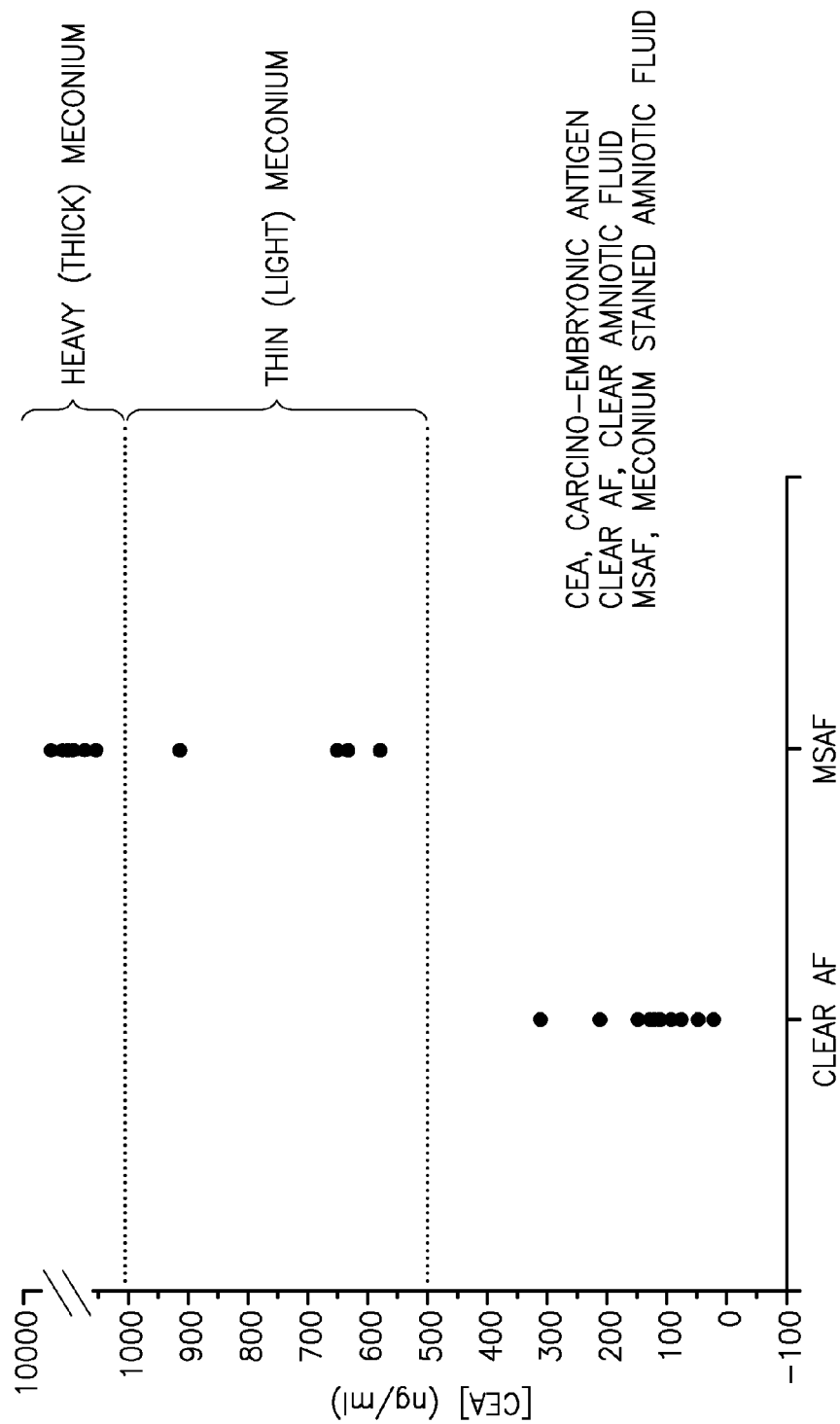
FIG. 5A is a graphical illustration of results of an experiment showing detection of meconium with different levels of CEA, in accordance with embodiments of the present invention.
Figure 5B:
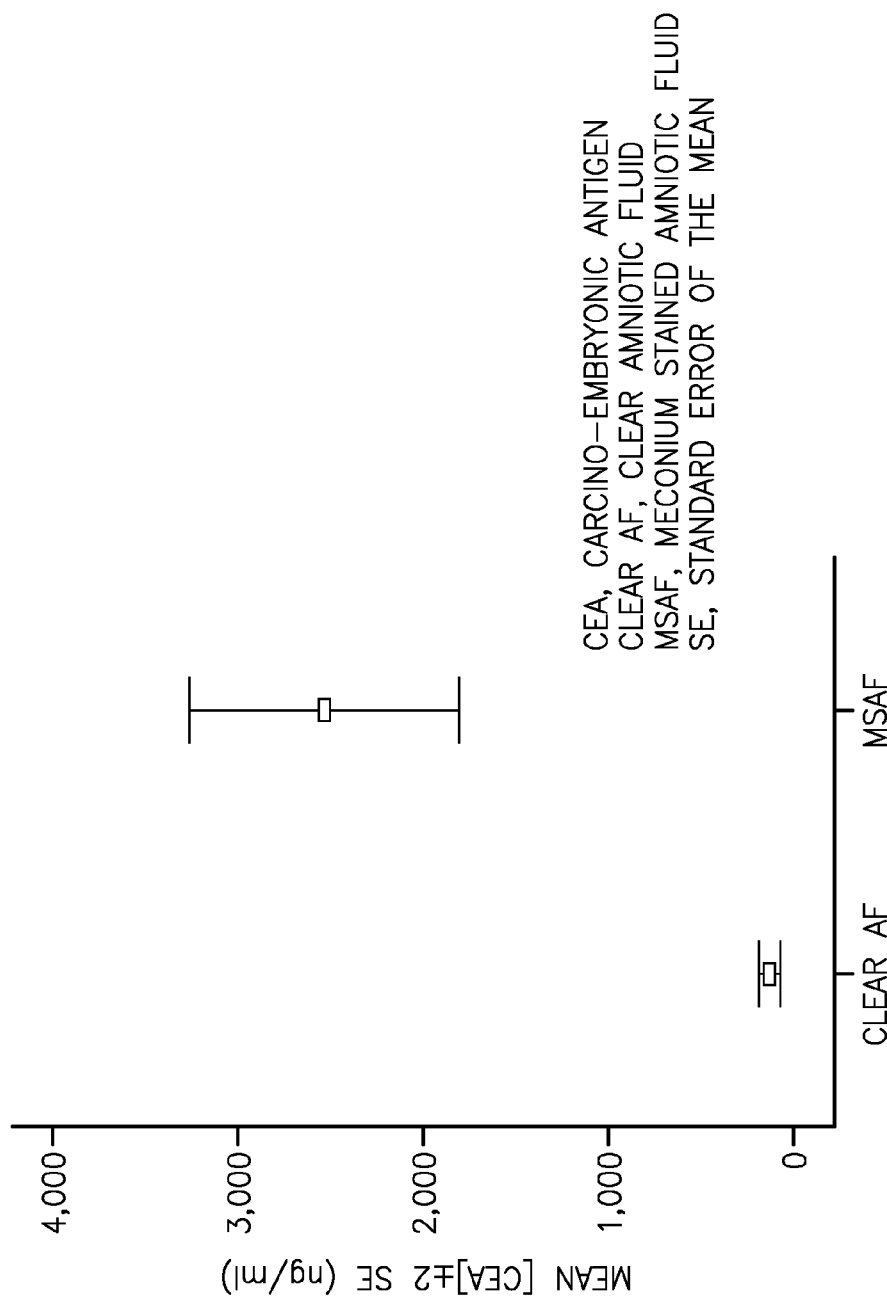
FIG. 5B is an additional graphical illustration of results of an experiment showing detection of meconium with different levels of CEA in accordance with embodiments of the present invention.
Figure 5D:
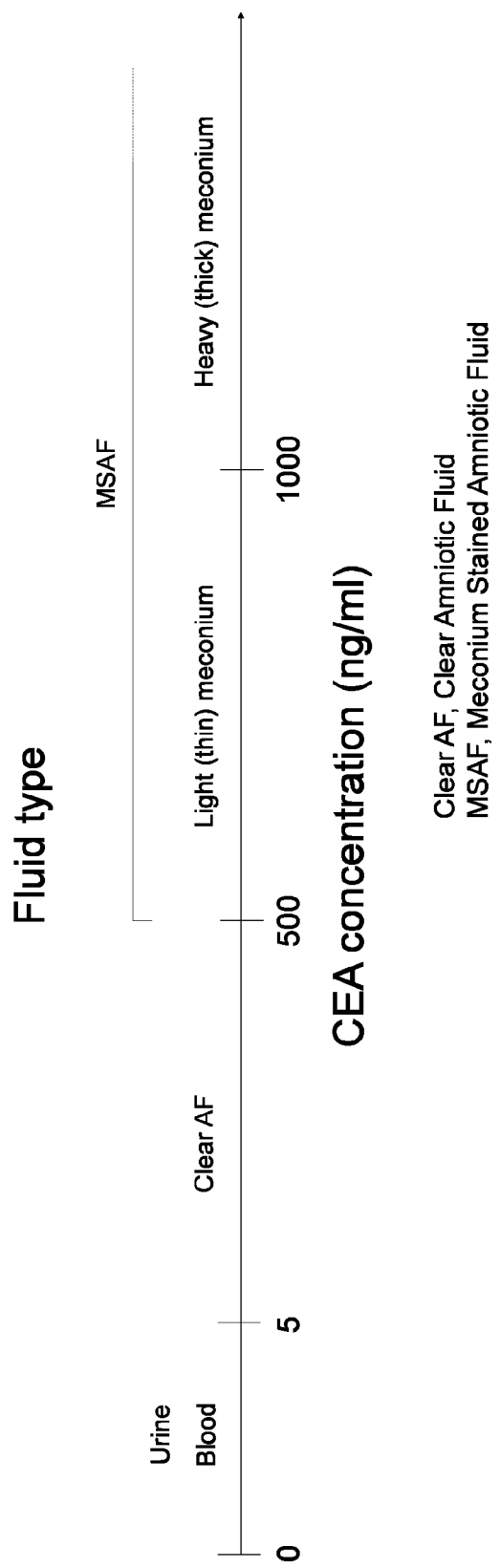
FIG. 5D is a graphical illustration showing multiple thresholds for CEA detection, providing a basis for determination of amniotic fluid, meconium and heavy meconium, in accordance with yet additional embodiments of the present invention.

Reference is also made to FIGS. 5A-5D, which are graphical illustrations of results of the Examples. The following conclusions were drawn from the above results:

1. CEA levels are 20 times higher in MSAF than in clear amniotic fluid and therefore CEA levels have diagnostic value in MSAF detection (FIG. 4B). The results are statistically significant (P value<0.001, student's t test).
2. In order to differentiate MSAF from clear amniotic fluid, the assay should have sensitivity threshold of around 500±100 ng/ml. Furthermore, the sensitivity threshold for heavy meconium can be determined at around 1000±200 ng/ml (FIG. 5A). Amniotic fluid AFP levels are not affected by meconium secretion.
3. Even in women with MSAF, urine CEA and AFP levels are in a normal range. Thus, through the measurement of CEA and/or AFP levels, involuntary urine secretion can be differentiated form clear amniotic fluid secretion or MSAF secretion (FIG. 5C)

The results of Phase I experiments show different sets of CEA levels in urine, clear AF and MSAF. AF CEA concentration is likely directly related to meconium concentration.

Even in urine of women with MSAF, CEA concentrations are within normal physiological limits. Therefore, CEA can serve both as an amniotic fluid marker and a MSAF marker as well as a thick MSAF marker. In order to do so, as shown in FIG. 4D, thresholds of 5 ng/ml; 500 ng/ml and 1000 ng/ml were shown to be effective for determining rupture of membranes (ROM), MSAF, and thick MSAF, respectively. The collection body 11 as shown in the embodiment of FIGS. 2A-2C may thus be comprised of a CEA detection agent with thresholds comparable or similar to the ones described herein.

Phase II of the experiment was then conducted to determine whether commercial assays available on the market for detection of cancer markers can be used for meconium detection in accordance with the present invention. Three potential problems were identified:

1. Normal serum/plasma levels of CEA are up to 5 ng/ml. Commercial assays are designed to detect CEA levels of 4-5 ng/ml and higher (detection threshold of 4-5 ng/ml) for the screening or follow-up of several malignancies. According to the results of Phase I, in order to differentiate MSAF from clear amniotic fluid, the assay should have a completely different threshold. As noted, this sensitivity threshold was determined to be around 500±100 ng/ml (~100 times fold).
2. The commercial assays are designed for serum or plasma specimens rather than for amniotic fluid specimens. Usually, serum has lower viscosity than amniotic fluid. Amniotic fluid expelled out from the uterus may contain heavy secretions (such as Vernix, mucus, and blood) and may have higher viscosity than serum or plasma. In order for the assay to be useful in the present invention, it would need to have independent ability to filter out these heavy secretions and do the sampling without the aid of any preceding manual procedure(s).
3. The commercial assays function under dry conditions only. The assay of the present invention must function under highly moist conditions. The assay's reagents and antibodies must somehow be isolated and protected from normal vaginal secretions and must be configured to react only upon rupture of membranes (ie, water breaking).

Phase II was conducted by first adjusting the commercially available assays as follows:

1. The threshold of the CEA chromatographic immunoassay was adjusted to be at 500±100 ng/ml.
2. The sampling region was covered with a "heavy secretions" filter. In this way, mucus, vernix and most red blood cells would not penetrate into assay's core or block the liquid component sampling process.
3. A partial seal was included: the sensitive immunoassay core (with color reagents and antibodies therein) was covered with adhesive translucent hydrophobic material. In the present experiment, nylon was used. In this way, the only exposed element was the specimen sampling region. Therefore, reagents were expected to flow in only one direction, even under highly moist conditions.

Results of Phase II were as follows:
A. Sampling with the Modified CEA Immunoassay:
1. All 10 clear amniotic fluid and 19 MSAF specimens gave negative and positive results for CEA, respectively.
2. Blood and urine samples of women with clear amniotic fluid or MSAF were negative to CEA (confirming experiment I results).

B. Sampling with the AFP Immunoassay:
1. All amniotic fluid specimens (clear and MSAF) were positive to AFP.
2. Urine samples of women with clear amniotic fluid or MSAF were negative to AFP (confirming experiment I results).

Results of Phase II indicate that modifications to existing assays for CEA must be made in order to render such assays usable for detection of meconium. Namely, a threshold for CEA levels for the purposes of the present invention should be approximately 500±100 ng/ml, and the use of a secretions filter and a partial seal are necessary and are feasible.

Phase III of this experiment involved testing a prototype. The partially sealed modified CEA immunoassays were built into custom designed pads (panty-liners, hygienic napkins etc.) that included heavy secretion filters. These pads were exposed to 100% air humidity conditions for 12 hours or were worn by female volunteers for 12-24 hours. Following these two exposures, the pads were inspected. After this time period, it was found that the reagents and antibodies remained protected and no lateral flow diffusion/reaction occurred. Afterwards, clear amniotic fluid or MSAF specimens were applied to the pads.

Results obtained were comparable to results obtained in Phase II of this experiment.

A pad or other collection body comprising these two assays has the following advantages: (1) Blood does not interfere with meconium detection by CEA and, therefore, light/heavy meconium masked by significant blood secretions can be identified. (2) Because AFP and CEA are not excreted into urine, the frequent dilemma of ROM vs. urinary incontinence in pregnant women can be easily solved: samples will be positive to AFP only or to AFP+CEA when ROM has occurred. Samples will be negative to AFP and to CEA if urine leak has occurred. According to U.S. Pat. No. 5,514,598, the 14 kilodalton protein (a proposed meconium marker) is present in urine and therefore cannot help with solving the dilemma above. Moreover, in comparison with CEA, the 14 kilodalton protein assay is less sensitive and specific for meconium. (3) Frequent sampling of amniotic fluid after ROM has occurred can reveal the time point of transition from meconium-free amniotic fluid to MSAF. This information can reveal the onset of fetal distress and necessitate exigent medical intervention (intrauterine resuscitation procedures, caesarean section, etc.).

Example 2

Amniotic Fluid and MSAF Detection

A commercial kit for detecting bile acid was purchased from Diazyme Laboratories (Poway, Calif., USA). Deoxycholic acid (DOC, a bile salt) was purchased from Sigma-Aldrich (St. Louis, Mo., USA). Accurate implementation of the procedure described by the Diazyme kit manual showed that the presence of DOC can be easily detected by the naked eye. DOC was applied to the solution containing the reconstituted kit reagents at room temperature. The original solution color is yellow. The presence of DOC initiated a two-stage reaction that led to a color change to dark red/brown after ten minutes. The presence of low DOC concentrations could be easily detected by the naked eye. Controls containing distilled water did not lead to any color change. Solutions maintained a stable color for approximately one hour. Meconium bile acids can be detected by the color change. A pH sensitive pad for the detection of amniotic fluid (Common-Sense Inc., Caesarea, Israel) can be combined with bile acid detection method.

Example 3

A Platform for Identifying Etiologies of Fetal Distress after ROM Occurs

High amniotic glucose level can be a result of uncontrolled gestational diabetes, which is a possible etiology for fetal distress. A colorimetric assay for glucose can be done by coupling the activities of the two enzymes: glucose oxidase and glucose peroxidase. In the first step, glucose oxidase catalyzes the reaction: glucose+oxygen→gluconolactone+hydrogen peroxide. In the second step, the hydrogen peroxide is used by the peroxidase to convert a chemical substrate (called a chromogen) from an uncolored form to a colored one. This reaction is used in commercial urinalysis kits. For example: the enzymes and the chromogen can be attached to the stick. When glucose is present, the reactions described above take place, and the stick changes color. In cases of early preterm premature rapture of membranes (PPROM; <32nd gestational week), the chances of placental abruption are as high as 10-15%. Benign abruption can last for days or weeks with mild maternal bleeding. However, placental abruption can be dynamic and exacerbate into significant maternal/fetal bleeding, and can be accompanied by fetal distress and meconium secretion. PPROM accruing before the 32nd gestational week is usually managed by close in-hospital expectant monitoring and attempts to avoid delivery. The rationale is to minimize early prematurity complications. However, exacerbation of placental abruption may lead to severe fetal distress and the need for an emergent cesarean section delivery. The occurrence of severe placental abruption can be identified by the appearance of MSAF together with fetal hemoglobin. Therefore, colorimetric assays for fetal hemoglobin and for CEA can help with the early diagnosis of placental abruption exacerbation.

In an attempt to identify the underlying cause for fetal distress, colorimetric assays for glucose, and maternal and fetal hemoglobin can be incorporated into the method according to the invention.

While this invention has been described in terms of some specific examples, many modifications and variations are possible. It is therefore understood that within the scope of the appended claims, the invention may be realized other than as specifically described. For example: immunochromatographic assays for squamous epithelium carcinoma associated Antigen (SCCA, WO2010150804), placental alpha-microglobulin-1 (PAMG-1; Phupong and Sonthirathi, 2012), CA-125 tumor marker, or AFP with Insulin-like growth factor binding protein-1 (IGFBP-1; WO2011151597) can replace AFP for the detection of ROM. The same applies for other materials (molecules, proteins, gut enzymes, bilirubin byproducts, intestinal wall plasmatic membrane transporters, etc.) that can replace bile acids or CEA for the detection of meconium.

What is claimed is:

1. A system for detection of meconium in amniotic fluid, the system comprising:
    a collection body for collecting a body fluid released from a vaginal opening of a pregnant woman; and
    a meconium detector positioned in said collection body, said meconium detector configured to detect presence of meconium in said collected body fluid.

2. The system of claim 1, wherein said collection body is at least one of: a hygienic pad, an underwear, a tampon or an applicator.

3. The system of claim 1, wherein said collection body comprises a front section; a back section; a middle section in between said front and back sections; and a top section spanning said front back and middle sections, said top section comprising an absorbent portion configured to absorb a body fluid.

4. The system of claim 3, wherein said absorbent portion is configured to absorb said body fluid in said front section, and wherein said meconium detector further comprises a strip for said body fluid to advance from said front section through said middle section and to said back section.

5. The system of claim 1, further comprising a fluid identifier positioned in said collection body, said fluid identifier configured for identifying said body fluid.

6. The system of claim 5, wherein said fluid identifier comprises at least one of: a detector for presence of alpha-fetoprotein or an acid-base indicator.

7. The system of claim 5, wherein said fluid identifier comprises a detector for CEA.

8. The system of claim 1, wherein said meconium detector is configured to detect an amount of CEA in said collected body fluid, and wherein a presence of meconium is indicated when said detected amount of CEA is above a pre-determined threshold.

9. The system of claim 8, wherein said pre-determined threshold is at least 300 ng/mL.

10. The system of claim 8, wherein said pre-determined threshold is approximately 500 ng/mL.

11. The system of claim 1, wherein said meconium detector is configured to detect an amount of CEA in said collected body fluid, and wherein a presence of heavy meconium is indicated when said detected amount of CEA is above a pre-determined heavy meconium threshold.

12. The system of claim 1, wherein said meconium detector further comprises a fluid-protective seal.

13. The system of claim 1, wherein said collection body further comprises a filter for heavy secretions.

14. The system of claim 1, wherein said meconium detector is configured to detect at least one of: a bile acid or a gut enzyme of fetal origin.

15. A system for detection of meconium in amniotic fluid, the system comprising:
    a collection body for collecting a body fluid released from a vaginal opening of a pregnant woman; and
    a meconium detector in fluid communication with said collection body for detecting meconium in said collected body fluid, said meconium detector comprising an immunoassay for CEA.

16. The system of claim 15, wherein said collection body is at least one of:
    a hygienic pad, an underwear, a tampon or an applicator.

17. The system of claim 15, wherein said meconium detector comprises a vial external to said collection body, said vial comprising at least one detecting reagent therein, wherein at least a portion of said collection body with the collected body fluid is brought into contact with said at least one detecting reagent in said vial.

18. The system of claim 17, wherein detecting reagent is configured to change color in the presence of a component of meconium.

19. The system of claim 15, wherein said immunoassay for CEA is set to detect CEA at a threshold of at least 300 ng/mL.

20. The system of claim 15, wherein said immunoassay for CEA further comprises a threshold for determination of heavy meconium.

* * * * *